United States Patent
Springob et al.

(10) Patent No.: US 6,482,808 B1
(45) Date of Patent: Nov. 19, 2002

(54) USE OF REDUCTIVE COMPOUNDS FOR STRENGTHENING AND IMPROVING THE STRUCTURE OF MATERIALS CONTAINING KERATIN

(75) Inventors: Christian Springob, Neu-Listernohl (DE); Manuela Javet, Marly (CH); Ursula Hehner, Brensbach (DE); Thomas Kripp, Fraenkisch-Crumbach (DE); Beate Grasser, Hattersheim (DE); Kirstin Uhl, Darmstadt (DE); Guenther Lang, Reinheim (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/700,871
(22) PCT Filed: Mar. 8, 2000
(86) PCT No.: PCT/EP00/02003
§ 371 (c)(1), (2), (4) Date: Jan. 23, 2001
(87) PCT Pub. No.: WO00/57839
PCT Pub. Date: Oct. 5, 2000

(30) Foreign Application Priority Data

Mar. 25, 1999 (DE) .......................................... 199 13 427

(51) Int. Cl.[7] .............................................. A01N 57/00
(52) U.S. Cl. ........................ 514/99; 514/474; 514/639; 514/703
(58) Field of Search .............................. 424/61; 514/99, 514/474, 693, 703

(56) References Cited

U.S. PATENT DOCUMENTS

| 5,162,303 A | 11/1992 | Goodman |
| 5,470,874 A | 11/1995 | Lerner |
| 5,660,818 A | 8/1997 | Dubief |
| 5,681,591 A | 10/1997 | Park |
| 5,981,578 A | 11/1999 | Alexandrides |

FOREIGN PATENT DOCUMENTS

| DE | 43 36 903 A | | 5/1995 |
| DE | 196 47 493 C | | 4/1998 |
| DE | 19647493 | * | 4/1998 |
| EP | 0 223 257 A | | 5/1987 |
| EP | 0 401 454 A | | 12/1990 |
| EP | 0 487 205 | | 5/1992 |
| EP | 0 493 985 A | | 7/1992 |
| EP | 0 589 373 A | | 3/1994 |
| EP | 0 607 642 A | | 7/1994 |
| GB | 1 603 639 A | | 11/1981 |
| WO | 86 01403 A | | 3/1986 |

* cited by examiner

Primary Examiner—Alton N Pryor
(74) Attorney, Agent, or Firm—Michael J. Striker

(57) ABSTRACT

The composition for hardening, strengthening and restructuring keratin-containing materials and/or for increasing the volume of keratin-containing fibers, such as hair, contains from 0.3 to 50.0% by weight of one or more reductones, each having a —(HO)C═C(OH)— group. The reductone ingredient is preferably ascorbic or isoascorbic acid, a salt of ascorbic or isoascorbic acid, such as an alkali metal or alkaline earth metal salt, an ester of ascorbic or isoascorbic acid, 6-O-palmitoyl ascorbate, ascorbyl phosphate, 2,3-dihydroxy-2-propenal and hydroxypropanedial. A method of treating keratin-containing materials or fibers to harden, strengthen and restructure keratin-containing materials and/or to increase the volume of the keratin-containing fibers by applying this composition and allowing it to act is described. A method of pre-treating keratin-containing material that is to be subjected to a chemical or physical treatment, such as dyeing or permanent shaping is also described.

18 Claims, No Drawings

USE OF REDUCTIVE COMPOUNDS FOR STRENGTHENING AND IMPROVING THE STRUCTURE OF MATERIALS CONTAINING KERATIN

This application is a 371 of PCT/EP00/02003 filed May 8, 2000.

BACKGROUND OF THE INVENTION

1. Field of the Invention

The present relates to 9 composition for hardening, strengthening and improving the structure (restructuring) materials containing keratin, especially damaged keratin fibers, as well as for the volume of fibers containing keratin, especially of human hair. The present invention also relates to a method for hardening, strengthening and improving the structure (restructuring) of material containing keratin, as well as a method for increasing the volume of fibers containing keratin.

2. Prior Art

Damage to keratin-containing materials due to environmental effects (such as high-energy irradiation), the physiological status (such as the age or health of the individual in question), mechanical and chemical effects are well known. The consequences are disadvantageous mechanical properties of the materials containing the keratin in question. Such damage of the internal structure of materials, containing keratin, is shown, for example, by the loss of hardness, strength, breaking strength, tear strength or bundle tensile strength.

In the case of keratinic fibers such as human hair, for example, such effects become noticeable especially by a lack of gloss, a reduced tear strength and poor combability. They are caused by aging processes, which are brought about physiologically, or induced by physical (weathering), mechanical (combing, brushing) and chemical effect. In the case of longer hair, these effects become noticeable particularly at the tips of the hairs. Chemical effects include, particularly, the bleaching, oxidative dyeing and permanent waving of hair, since these inherently aggressive oxidation or reducing agents show their full effect moreover mostly only in a strongly alkaline medium. However, other chemical influences, such as water containing chlorine or salts, also develop harmful defects on materials containing keratin.

The tear strength measurement is a conventional method for measuring the degree of damage to the hair. For this, a tension and extension measuring device is used to measure the force, which is required to tear individual hairs. From these individual, measured values of the tear strength, the so-called bundle tensile strength (BTS) is determined in that, initially, the tear strength for a hair diameter of 0.08 mm (average diameter) is calculated from the individual values, taking into consideration the respective hair diameter. By including the hair density, the data is finally converted into units of bundle tensile strength (cN/dtex). The larger the numerical value of the tear strength or the bundle tensile strength, the less is the damage to the hair.

SUMMARY OF THE INVENTION

Conventional commercial rinses and cures contain, as active substances, mainly cationic surfactants or polymers, waxes and/or oils. The greater the damage to the hair, the larger is the number of anionic groups at the surface. Cationic compounds are attracted electrostatically to oppositely charged surface, whereas oils and waxes interact with the hydrophobic groups of the keratin. An improvement in the structure of the interior of the hair can therefore not be attained with these care products.

It was therefore an object of the present invention to make available a preparation, especially a cosmetic preparation, which eliminates the disadvantages mentioned above.

Pursuant to the invention, this objective attained with a preparation containing at least one reducing, aliphatic or cyclic compound containing the grouping of atoms —(HO)C=C(OH)—, including its isomeric forms, as well as its salts and esters, as a means for hardening, strengthening and restructuring materials containing keratin.

The use, for example, of ascorbic acid in hair care agents or hair dyeing agents is known. For example, it is proposed in the European patent 0 401 454 to remove residue of hydrogen peroxide, which remain behind in human hair after an oxidative treatment, with an aqueous solution of ascorbic acid. Suitable for this are effervescent tablets, which contain ascorbic acid and are dissolved immediately before use in water, which is then used for rinsing the hair.

Furthermore, ascorbic acid is used in the German Offenlegungsschrift 1 444 2 1b in a liquid hair dyeing agent, in order to stabilize the otherwise unstable liquid agent. The oxidation hair dyeing agent of the German Offenlegungsschrift 3 642 097 also contains ascorbic acid as stabilizer.

All the more surprising was the finding that ascorbic acid can be used for improving the structure (hardening, strengthening, restructuring) of materials containing keratin, especially of fibers containing keratin, such as human hair.

Surprisingly, it was found that, due to the use of a preparation containing at least one reducing, aliphatic or cyclic compound, which contains an endiol of the grouping of atoms —(HO)C=C(OH)—, including its isomeric forms, as well as its salts and esters, changes the structure of keratin-containing materials (skin appendages such as keratin fibers, hair or nails) in such a manner, that a hardening, strengthening, increase in the breaking strength, tear strength or bundle tensile strength of the material in question takes place.

In association with this, not only does a restructuring (repair) of materials containing damaged keratin become possible, but also a protective effect, which counteracts damage to these materials before or during an exposure to appropriate noxious agents and is also capable of preventing or reducing the severity of such damage.

Aside from these harmful changes, which are brought about by exogenous noxious agents, the inventive use can also develop advantageous effects in conditions or changes in the structure of keratin-containing the materials, brought about by physiological processes, such as, material (hair or nails), containing keratin that is brittle due to aging, or fine hair, which may be inherited or acquired due to aging (baby hair, hair of old age).

Associated with this, it was furthermore possible to establish that, in the case of keratinic fibers, especially in the case of hair, an increase in volume, which may have an advantageous effect in hair styling, can be achieved by the inventive use. It is suspected that the action of increasing the volume is related causally with the hair hardening, hair strengthening or the hair restructuring action of the inventive composition.

Accordingly, the object of the present invention is the use of at least one reducing, aliphatic or cyclic compound, individually or as a mixture, containing the atomic grouping

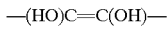

including its isomeric forms, as well as its salts and esters, in a composition for hardening, strengthening and restructuring materials containing keratin.

The isomeric forms of these atomic groupings, containing the aliphatic and cyclic compounds in question, comprise epimeric and tautomeric forms.

Pursuant to the invention, preferably reductones are used.

The present invention also includes a method for hardening, strengthening and restructuring materials containing keratin and/or for increasing the volume of fibers containing keratin, wherein a composition, containing at least one atomic grouping

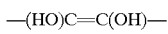

containing at least one reducing aliphatic, or cycling compound, including its isomeric forms, as well as its salts and esters, is brought into contact with the material, containing the keratin to be treated, and remains there after the application or is rinsed off or out after a suitable period of action with an aqueous agent.

Further embodiments of the present invention are given in the dependent claims.

Advantageously, for example, ascorbic acid or isoascorbic acid or its salts or esters, such as 6-O-palmitoyl ascorbate, ascorbyl phosphate, hydroxypropandial (triose reductone), 2,3-dihydroxy-2-cyclopenten-1-one (reductic acid), or mixtures of these compounds, can be used. The use of ascorbic acid or isoascorbic acid, especially ascorbic acid, is preferred.

When salts of ascorbic acid or isoascorbic acid are used, the free acid can also be produced in situ from the salts, such as the alkali metal ascorbates or alkaline earth metal ascorbates or the alkali metal isoascorbates or alkaline earth metal ascorbates, by the addition of a physiologically tolerated acid (such as citric acid, glyoxylic acid, 2-oxo glutaric acid, lactic acid, tartaric acid, acetic acid). This is of advantage because of the better solubility of the salts in water, especially at higher concentrations. Especially the calcium salt, the magnesium salt and the sodium salt of ascorbic or isoascorbic acid come into consideration here as ascorbic salt or isoascorbic salt.

As already stated, any combination of the aforementioned, reducing aliphatic and/or cyclic compounds can be used for the purpose given. Preferred is the use of the combination of ascorbic or isoascorbic acid or its salts or esters, such as 6-O-palmitoyl ascorbic acid, ascorbyl phosphate, hydroxypropandial (triose reductone), 2,3-dihydroxy-2-cyclopenten-l-one (reductic acid), or mixtures of these compounds, for hardening, strengthening, improving the structure (restructuring) and increasing the volume, particularly of structure-damaged materials containing keratin, especially fibers containing keratin, such as hair.

With regard to the stability or shelf life, it may be of advantage if the reducing aliphatic and/or cyclic compound, on which the invention is based, is enveloped by a protective layer. For such a case, cellulose-enveloped or silicone-enveloped compounds come into consideration. For example, the silicone-enveloped ascorbic acid, obtainable under the name SC or the ethylcellulose-enveloped ascorbic acid, obtainable under the name EC from Hoffmann LaRoche Basel.

As preferred amounts, 0.3 to 50% by weight and especially 0.5 to 10% by weight of the reducing, aliphatic and/or cyclic compound in question can be used.

The composition, described for the inventive use, may be contained in any suitable formulation, which is known in the cosmetics or pharmaceutical industry. In particular, the composition may be an aqueous or aqueous alcoholic solution, a gel, a cream, or an emulsion or a foam, the composition being produced in the form of a single component preparation as well as in the form of a multi-component preparation.

In the case of a single component preparation, the composition may contain at least one reducing aliphatic and/or cyclic compound of the present invention, (such ascorbic acid, isoascorbic acid, sodium ascorbate) together with suitable inert and carrier materials (such as thickeners, acids, fragrances, solvents, salts, wetting agents, UV absorbers).

If the composition is in the form of a multi-component preparation, it may consist of at least two different components, which are separated spatially from one another, until they are used. A first component may contain either the reducing, aliphatic and/or cyclic compound (active ingredient) of the present invention alone or the active ingredient may be present together with an inert material (such as a thickening agent), advantageously in solid dry form (for example, as a powder, either pressed or not pressed, as a granulate or as tablets) in admixture with this first component. A second or further component contains only inert materials and carrier materials.

It is, however, also possible that different components of different inventive, active ingredients are contained either individually or as a mixture in a multi-component preparation, either by themselves or simultaneously together with different inert materials and that the other component contains only inert materials and carriers.

With respect to handling and stability (shelf life), a multi-component preparation of the active ingredients, on which the invention is based, may be of advantage.

The invention therefore also comprises the use of a composition, wherein the composition is present as a one-component preparation or as a multi-component preparation, the composition of the one-component preparation containing at least one reducing, aliphatic and/or cyclic compound together with inert materials and additives and the composition in the multi-component preparation comprising a first component, which contains at least one reducing, aliphatic and/or cyclic compound with or without inert ingredients and additives and that a second component contains only inert ingredients and additives, or the composition in the multi-component preparation comprising at least three different components, of which at least two contain at least one, in each case different, reducing, aliphatic and/or cyclic compound and that at least on further component contains only inert ingredients and additives.

It is, of course, obvious that, to prepare a ready-for use composition or preparation, the spatially separate individual components of a multi-component preparation must be mixed shortly before the inventive use.

Aside from being produced in powder form, the inventive composition, as protection against the formation of dust, can also be prepared as tablets—even as effervescing tablets—or as granulate. Before use, the composition is then prepared from this with cold or water, optionally with the addition of one or more of the inert ingredients named below. It is, however, also possible that these inert ingredients (provided that they are present in solid form) are already contained in the powder or granulate or in the effervescing tablet. Dust formation can be reduced additionally by wetting the powder with oils or waxes.

The composition, on which the invention is based, may contain additional inert ingredients, such as solvents, like water, low molecular weight aliphatic alcohols, such as ethanol, n-propanol and isopropanol, glycol ethers or glycols, such as glycerin and, in particular, 1,2-propylene glycol, furthermore wetting agents or emulsifiers from the classes of anionic, cationic, amphoteric or nonionic surface active substances, such as fatty alcohol sulfates, ethoxylated fatty alcohol sulfates, alkyl sulfonates, alkylbenzenesulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated fatty acid esters, furthermore thickeners, such as higher molecular weight fatty alcohols, starch or cellulose derivatives, thiols, ketocarboxylic acids (oxocarboxylic acids), particularly α-ketocarboxylic acids or their physiologically tolerated salts, UV absorbers, perfumes, dyes, hair pre-treating agents, conditioners, hair swelling agents, preservatives, Vaseline, paraffin oil and fatty acids, as well as other care agents such as cationic resins, lanolin derivatives, cholesterol, pantothenic acid and betaine.

The pH of the composition preferably is about 1.8 to 7.0 and especially 3.0 to 6.5. If necessary, the pH can be adjusted to the desired value by the addition of further acids such α-hydroxycarboxylic acids, like lactic acid, tartaric acid, citric acid or malic acid, phosphoric acid, acetic acid, glycolic acid, salicylic acid, glutathione, or gluconic acid lactone, or of alkalizing agents such as alkanolamines, alkylamines, alkali hydroxides, ammonium hydroxides, alkali carbonates, ammonium carbonates or alkali phosphates.

The composition can either remain at the site of the application, that is, after it is brought into contact with the material containing the keratin to be treated, or removed once again after a period of action of one minute up to about one hour at a temperature between 20° C. and about 60° C. The method depends on the nature of the material to be treated and can therefore be varied.

In the event that the use is directed to a method for the treatment of fibers containing keratin, the composition may also remain there (for example, in the hair) or be rinsed out once again after use. In the latter case, the period of action of the composition depends on the temperature (about 20° to 50° C.) and is 1 minute to 60 minutes and especially 5 minutes to 20 minutes, it being possible to accelerate the repair action (hardening, restructuring, optionally the therewith associated increase in volume) by supplying heat and, at the end of the period of action, the hair is rinsed with water and optionally washed with a shampoo. The inventive composition can also be used as a pre-treating agent before dyeing the hair or before a permanent wave treatment, in order to prevent damage to the hair by these oxidative treatments.

It was possible to note that the inventive use of at least one of the aliphatic and/or cyclic compounds described or the inventive method of the present invention makes possible a clear improvement in the structure of fibers containing previously damaged keratin, an improvement, which can be confirmed by a statistically highly significant increase in the tear strength.

The following examples are intended to explain the object in greater detail, without limiting it to these examples.

Unless stated otherwise, all the percentages, given in the specification, relate to the total weight of the respective composition.

EXAMPLE 1

Repair Gel

| Component A: | |
| --- | --- |
| ascorbic acid | 5.00 g |
| methylhydroxyethylcellulose (Tylose MHB 10,000P of Hoechst/Germany) | 1.50 g |
| Component B: | |
| citric acid | 5.00 g |
| trisodium citrate dihydrate | 0.80 g |
| PEG-35 castor oil | 0.30 g |
| sodium formate | 0.30 g |
| water | 93.60 g |

The components A and B are added together and shaken well. The gel forming was allowed to act for 15 minutes at 40° C. under a plastic covering on a bleached strand of hair. Subsequently, the bundle tensile strength was compared with that of a bleached, but otherwise untreated strand. The following values were obtained for the bundle tensile strength in cN/tex:

BZF/(cN/tex]) standard bleached strain: 11.6

BZF/(cN/tex) bleached strain, treated with a repair gel: 13.7

EXAMPLE 2

Repair Balsam

| Component A: | |
| --- | --- |
| cetyl stearyl alcohol | 1.40 g |
| glyceryl stearate | 0.7 g |
| Ceteareth-20 | 0.1 g |
| cetyltrimethylammonium chloride | 0.6 g |
| aromatic acid | 0.5 g |
| perfume | 0.4 g |
| water, fully desalinated | 91.3 g |
| Component B: | |
| ascorbic acid | 5.00 g |

The components A and B are added together and shaken well. The gel forming was allowed to act for 15 minutes at 40° C. under a plastic covering on a bleached strand of hair. Subsequently, the bundle tensile strength was compared with that of a bleached, but otherwise untreated strand. The following values were obtained for the bundle tensile strength in cN/tex:

BZF/(cN/tex]) standard bleached strain: 15.5

BZF/(cN/tex) bleached strain, treated with a repair gel: 16.4

EXAMPLE 3

Repair Gel

| ascorbic acid | 5.00 g |
| --- | --- |
| methylhydroxyethylcellulose (Tylose MHB 10,000P of Hoechst/Germany) | 1.50 g |

-continued

| | |
|---|---|
| trisodium citrate dihydrate | 0.30 g |
| water | to 100.00 g |

EXAMPLE 4

Repair Gel

| | |
|---|---|
| isoascorbic acid | 5.00 g |
| methylhydroxyethylcellulose (Tylose MHB 10,000P of Hoechst/Germany) | 1.50 g |
| water | to 100.00 g |

The pH was adjusted to a value of 3.0 to 6.0 with trisodium citrate dihydrate.

EXAMPLE 5

Repair Gel

| | |
|---|---|
| sodium ascorbate | 5.60 g |
| methylhydroxyethylcellulose (Tylose MHB 10,000P of Hoechst/Germany) | 1.50 g |
| citric acid | 5.00 g |
| water | to 100.00 g |

EXAMPLE 6

Repair Stay-in Spray Cure

| | |
|---|---|
| Component A: | |
| stearyl alcohol | 0.3 g |
| glyceryl stearate | 0.16 g |
| Ceteareth-20 | 0.1 g |
| PHB-methylester | 0.1 g |
| perfume | 0.2 g |
| ethanol | 5.0 g |
| water | 93.3 g |
| Component B: | |
| ascorbic acid | 5.0 g |

Components A and B were added together and shaken well. The resulting solution was sprayed on the hair, combed in and remained there.

EXAMPLE 7

Repair Gel

| | |
|---|---|
| sodium ascorbate | 6.00 g |
| citric acid | 6.00 g |
| hydroxyethylcellulose | 1.50 g |
| glyoxylic acid | 0.50 g |
| water | to 100.00 g |

The pH of the repair gel was between 3.0 and 6.0.

EXAMPLE 8

Repair Gel

| | |
|---|---|
| isoascorbic acid | 6.00 g |
| methylhydroxyethylcellulose (Tylose MHB 10,000P of Hoechst/Germany) | 1.50 g |
| cysteine | 2.00 g |
| 2-oxoglutaric | 0.80 g |
| water | to 100.00 g |

The pH was adjusted to a value of 3.0 to 6.0 with trisodium citrate dihydrate.

EXAMPLE 9

Repair Gel

| | |
|---|---|
| sodium ascorbate | 5.70 g |
| L-cysteine | 2.00 g |
| magnesium sulfate | 1.00 g |
| citric acid | 7.40 g |
| trisodium citrate dihydrate | 1.00 g |
| hydroxyethylcellulose | 1.50 g |
| 2-oxoglutaric acid | 0.80 g |
| water | to 100.00 g |

EXAMPLE 10

Repair Gel

| | |
|---|---|
| sodium ascorbate | 5.70 g |
| L-cysteine | 2.00 g |
| magnesium sulfate | 1.00 g |
| citric acid | 7.40 g |
| trisodium citrate dihydrate | 0.60 g |
| hydroxyethylcellulose | 1.50 g |
| oxalic acid | 0.50 g |
| water | to 100.00 g |

EXAMPLE 11

Repair Gel

| | |
|---|---|
| sodium ascorbate | 5.70 g |
| L-cysteine | 2.00 g |
| magnesium sulfate | 1.00 g |
| citric acid | 7.40 g |
| trisodium citrate dihydrate | 1.00 g |
| hydroxyethylcellulose | 1.50 g |
| oxalic acid | 0.70 g |
| water | to 100.00 g |

The above-described repair gel was applied on the damaged hair and allowed to act in each case for 15 minutes for 40° C. under a plastic cover. After that, the hair was washed thoroughly with water and shampoo, rinsed with water and then dried.

EXAMPLE 12

Repair Balsam for Bleached Hair

| Component A: | |
|---|---|
| stearyl alcohol | 1.40 g |
| petrolatum | 1.40 g |
| glyceryl stearate | 0.7 g |
| Ceteareth-20 | 0.05 g |
| cetyltrimethylammonium chloride | 0.6 g |
| aromatic acid | 0.5 g |
| perfume | 0.4 g |
| water, fully desalinated | 94.95 g |
| Component B: | |
| ascorbic acid | 5.00 g |

Components A and B were added together and shaken well. The cure was allowed to act on the hair for 15 minutes at 40° C.

What is claimed is:

1. A method of hardening, strengthening, restructuring keratin-containing material and of increasing volume of keratin fibers when said keratin-containing material comprises said keratin fibers, in order to repair or prevent damage to said keratin-containing material, said method comprising the steps of:

a) providing a composition having a pH of from 3.0 to 7.0 and consisting essentially of water, at least one reductone and, optionally, at least one optional ingredient, wherein said at least one reductone is selected from the group consisting of ascorbic acid, salts of ascorbic acid, esters of ascorbic acid, isoascorbic acid, salts of isoascorbic acid, esters of isoascorbic acid, 6-O-palmitoyl ascorbate, ascorbyl phosphate, 2,3-dihydroxy-2-propenal and hydroxypropanedial and wherein said at least one optional ingredient is selected from the group consisting of solvents, thickeners, pH adjusting agents, wetting agents, emulsifiers and perfumes;

b) bringing the composition of step a) into contact with said keratin-containing materials;

c) after step b), allowing said composition to remain on said keratin-containing materials for a predetermined time interval; and d) after step c), rinsing said composition out from said keratin-containing materials after said predetermined time interval with an aqueous rinsing agent;

whereby said damage to said keratin-containing materials is effectively repaired or prevented.

2. The method as defined in claim 1, wherein said keratin-containing materials consist of hair and said damage is due to exposure of said hair to environmental influences or physiological status.

3. The method as defined in claim 1, wherein said keratin-containing materials consist of hair and said damage is due to a chemical or mechanical treatment.

4. The method as defined in claim 3, wherein said chemical or mechanical treatment is oxidative dyeing of the hair, bleaching of the hair or permanent waving of the hair.

5. The method as defined in claim 1, wherein from 0.5 to 10.0 percent by weight of said at least one reductone is present in said composition.

6. The method as defined in claim 5, wherein said composition is in the form of an aqueous emulsion, foam, cream or gel and said thickeners consist of fatty alcohols, starch, hydroxyalkylcellulose and alkylhydroxyalkylcellulose compounds, wherein said alkyl groups have one or two carbon atoms.

7. The method as defined in claim 1, wherein said salts of ascorbic acid and said salts of isoascorbic acid are sodium salts, magnesium salts or calcium salts.

8. The method as defined in claim 1, wherein said at least one reductone is said ascorbic acid and said ascorbic acid is present in said composition in the form of silicone-enveloped ascorbic acid or hydroxyethylcellulose-enveloped ascorbic acid in order to provide increased storage stability.

9. The method as defined in claim 1, wherein said predetermined time interval is from 5 minute to 20 minutes and said keratin-containing materials are brought into contact with said composition at a temperature from 20° C. to 50° C.

10. A repair gel for hardening, strengthening, restructuring keratin-containing material and for increasing volume of keratin fibers when said keratin-containing material comprises said keratin fibers, in order to repair or prevent damage to said keratin-containing material, said composition having a pH of 3.0 to 7.0 and consisting essentially of:

water or water and at least one alcohol;

from 0.3 to 50 percent by weight of at least one reductone and, optionally, at least one optional ingredient, wherein said at least one reductone is selected from the group consisting of ascorbic acid, salts of ascorbic acid, esters of ascorbic acid, isoascorbic acid, salts of isoascorbic acid, esters of isoascorbic acid, 6-O-palmitoyl ascorbate, ascorbyl phosphate, 2,3-dihydroxy-2-propenal and hydroxypropanedial and wherein said at least one optional ingredient is selected from the group consisting of solvents, pH adjusting agents, wetting agents, emulsifiers and perfumes; and a thickener selected from the group consisting of fatty alcohols, starch, hydroxyalkylcellulose and alkylhydroxyalkylcellulose compounds, wherein said alkyl groups have one or two carbon atoms.

11. The repair gel as defined in claim 10, wherein said salts of ascorbic acid and said salts of isoascorbic acid are sodium salts, magnesium salts or calcium salts.

12. The repair gel as defined in claim 10, wherein said at least one reductone is said ascorbic acid and said ascorbic acid is present in the form of silicone-enveloped ascorbic acid or hydroxyethylcellulose-enveloped ascorbic acid in order to provide increased storage stability.

13. A composition for hardening, strengthening, restructuring keratin-containing material and for increasing volume of keratin fibers when said keratin-containing material comprises said keratin fibers, in order to repair or prevent damage to said keratin-containing material, said composition having a pH of 3.0 to 7.0 and consisting essentially of:

water or water and at least one alcohol;

from 0.3 to 50 percent by weight of at least one reductone and, optionally, at least one optional ingredient, wherein said at least one reductone is selected from the group consisting of ascorbic acid, salts of ascorbic acid, esters of ascorbic acid, isoascorbic acid, salts of isoascorbic acid, esters of isoascorbic acid, 6-O-palmitoyl ascorbate, ascorbyl phosphate, 2,3-dihydroxy-2-propenal and hydroxypropanedial and wherein said at least one optional ingredient is selected from the group consisting of solvents, pH adjusting agents, wetting agents, emulsifiers and perfumes; and a thickener selected from the group consisting of fatty alcohols, starch, hydroxyalkylcellulose and alkylhydroxyalkylcellulose compounds, wherein said alkyl groups have one or two carbon atoms.

14. The composition as defined in claim 13, wherein said salts of ascorbic acid and said salts of isoascorbic acid are sodium salts, magnesium salts or calcium salts.

15. The composition as defined in claim 3, wherein said at least one reductone is said ascorbic acid and said ascorbic acid is present in the form of silicone-enveloped ascorbic acid or hydroxyethylcellulose-enveloped ascorbic acid in order to provide increased storage stability.

16. The composition as defined in claim 13, in the form of a gel, an emulsion, a foam and a cream.

17. The composition as defined in claim 13, made by mixing at least two components stored separately, wherein one of said at least two components consists essentially of said at least one reductone; and wherein at least one other of said at least two components consists essentially of said water or said water and said alcohol and said at least one optional ingredient.

18. The composition as defined in claim 13, wherein said at least one reductone is selected from the group consisting of said salts of said ascorbic acid and said salts of said isoascorbic acid and a free acid is generated by addition of an acid in situ to said at least one reductone.

* * * * *